United States Patent [19]
Liegeois

[11] Patent Number: 5,652,053
[45] Date of Patent: Jul. 29, 1997

[54] HOMOGENOUS AND FLEXIBLE OR RIGID COMBINATIONS OF MATERIALS MOLDABLE AND ADHESIVE AT TEMPERATURE BELOW 90°C

[76] Inventor: Jean Marie Liegeois, 411 Moulin de Wadeleux, B-4654, Herve, Belgium

[21] Appl. No.: 397,086

[22] PCT Filed: Sep. 7, 1993

[86] PCT No.: PCT/BE93/00055

§ 371 Date: Mar. 7, 1995

§ 102(e) Date: Mar. 7, 1995

[87] PCT Pub. No.: WO94/05338

PCT Pub. Date: Mar. 17, 1994

[30] Foreign Application Priority Data

Sep. 7, 1992 [BE] Belgium .................................. 9200786

[51] Int. Cl.$^6$ .............................. C08L 33/06; C08L 67/04; C08L 75/04; A61F 5/01
[52] U.S. Cl. ..................... 442/150; 427/2.31; 427/208.2; 427/389.9; 525/131; 525/411; 525/412; 525/415; 525/440; 525/445; 525/903; 602/2
[58] Field of Search ............................ 428/290; 525/412, 525/903, 445, 131, 411, 415, 440; 427/2.31, 208.2, 389.9; 602/2

[56] References Cited

U.S. PATENT DOCUMENTS

| | | | |
|---|---|---|---|
| 3,760,034 | 9/1973 | Critchfield | 325/12 |
| 4,326,509 | 4/1982 | Usakura | 128/90 |
| 4,404,333 | 9/1983 | Watanabe | 428/290 |
| 4,912,174 | 3/1990 | Grouiller | 525/415 |

FOREIGN PATENT DOCUMENTS

| | | |
|---|---|---|
| 0086686 | 8/1983 | European Pat. Off. . |
| 0169037 | 1/1986 | European Pat. Off. . |
| 0235500 | 9/1987 | European Pat. Off. . |
| 0443759 | 8/1991 | European Pat. Off. . |
| 2021600 | 12/1979 | United Kingdom . |
| 9109909 | 7/1991 | WIPO . |

*Primary Examiner*—Patricia A. Short
*Attorney, Agent, or Firm*—John F. A. Earley; John F. A. Earley, III

[57] ABSTRACT

Combinations of IPN type molecular or intramolecular materials, which are thermoadhesive at temperatures not exceeding 90° C. and which can be molded and shaped at said temperature, are characterized in that they contain a first rubber-like elastoviscous constituent having a softening point not exceeding 90° C. and a second, semi-cristalline constituent essentially of the polyester type having a fusion temperature of 35° to 80° C. These combinations have controlled adhesiveness and adequate fluidity for application by hand particularly in do it yourself applications, orthopedics, sport and physiotherapy, and as an adhesive material on rough or porous bodies.

25 Claims, No Drawings

HOMOGENOUS AND FLEXIBLE OR RIGID COMBINATIONS OF MATERIALS MOLDABLE AND ADHESIVE AT TEMPERATURE BELOW 90°C

This invention relates to new alloys under various forms of interpenetrating polymer networks (IPN), principally under the form of semi-IPN or thermoplastic IPN, in sheets, plaques or bulk product that are thermomoldable and thermoadhesive, flexible or rigid, with rather short setting time, and to preparation processes of those alloys and to processes for their eventual application on a textile substrate.

Besides usual applications of plastics, there are various potential domains of applications wherein it is required to realize at every occasion a unique part or assembly with a material that one desires to mold, form or shape preferably manually and with a simple pretreatment such as heating at an easily accessible temperature. It may also concern a matter one desires to apply between two objects showing uneven surfaces in order to bond them together and where in particular usual adhesives are not suited because there are cavities to fill for example.

Through the preparation treatment for their use, those materials must therefore have an adequate malleability as well as an adhesive potential to themselves and eventually to other bodies. The herein envisioned preparation treatment is limited to a temperature conditioning which will be detailed later, excluding the use of any solvent or external adhesive.

The application being in view can bear on an object or a creation as rigid as possible or one can seek in the application for some degree of flexibility to be selected according to the situation.

Such applications are often sought by individuals having not necessarily a great dexterity, who are willing to practice themselves without sophisticated technical means, realizing the molding, the shaping or the assembly principally by hand with the eventual help of a few simple tools such as scissors, clamps and holders. Obviously, the applications in view here can also be practiced by professionals operating in an industrial environment but that is not required.

As a result those forming, molding, bonding applications must be realized from a pretreatment temperature that remains accessible without risk of burns or other disadvantage that may cause clumsiness or an accident.

The used material must lose its adhesive property once it returns to ambient temperature and also keep the shape it was given and it must be capable to withstand mechanical stresses to which it may be exposed and not lose its shape up to a temperature governed by the application.

A pretreatment temperature range from 40° C. to 80° C. seems to be suitable, in any case under 100° C. so that such preparation can be done easily and relatively quickly by using hot water for example. It makes sense that alternative heating sources can be used such as the thermal oven, the heat gun or the microwave oven.

Considering the applications in view, it is also recommended that those materials are inert and do not release substances that are toxic, irritating or with another noxious character so that the user can apply them without any particular safety mean.

Those products must also be stable for a long period of time without being subject neither to chemical aging nor preferably to any physical aging.

Therefore it should not be necessary to have to use sophisticated packaging such as hermetically sealed pouches subjected to tearing and that compromise the use of the material once the pouch has been opened.

There are already a few domains of applications of the type of product addressed by this invention where one uses materials that are thermoformable and thermoadhesive or not as from a temperature of treatment from about 70° C. to 80° C. and that are essentially restricted to uses where a high rigidity is looked for. This concerns principally the physiotherapy where splints, orthoses and other means of support are already made like that, the orthopedics interested with said thermoplastic bandages for cylindrical casting or with external prostheses made of same material, but also the field of decoration where stage scenery, masks and various objects essentially in three dimensions are made like that.

In order to obtain the property of formability only, after treatment at about 70°–75° C., one knows today the trans 1–4 polyisoprene, better known in particular under the trademark "ORTHOPLAST", and which allows to realize splints and orthoses with much ease due to the good moldability of trans 1–4 polyisoprene in the melt state. However, the trans 1–4 polyisoprene does not exhibit adhesiveness neither on itself nor on other object and it is necessary to use chloroform to bond two parts together.

In order to obtain the effect of both formability and adhesiveness in the desired temperature range, one has also linear polymers of cyclic esters characterized by "COO" moieties apart one to another with methylene radicals comprising 2 to 7 carbon atoms of which the principal available representative is the polymer of 2-oxepanone better known under the popular name of polycaprolactone (PCL). The U.S. Pat. No. 3,692,023 suggests the use of that polymer to obtain immobilization devices. In other respects, the U.S. Pat. No. 4,273,115 recommends a particular Raschel knitted web partially impregnated with that PCL polymer having a molecular weight of about 40 000 as material for cylindrical casting. Finally, in the U.S. Pat. No. 4,316,457, one has proposed the preparation of a linear thermoplastic polyurethane synthesized in two steps where a prepolymer based on two moles of diisocyanate and one mole of polyester diol is added with one mole of polyester diol prior to impregnation of a Raschel knitted web to build chain extension while completing the polymerization on the latter at same time as the solvent is removed.

As they are described, those polyesters become fluid at the melt temperature and have an excessive adhesiveness on any object to which they come in contact in the melt state. This adhesiveness in the melt state that leads to transfer of material does nevertheless disappear after hardening under cooling. Therefore the use of those polyesters has required various adaptations that can be classified in three categories.

The first category refers to the use of external means. In the U.S. Pat. No. 3,692,023, one uses a soft under-layer to keep the polymer out of sticking to the skin and hair that it covers when it is applied onto. In the same Patent, it is considered to press the same polymer in sheets on a support or as a sandwich made of a knitted, woven or non-woven fabric with the assigned role is to prevent the flow of the material in the melt state. In the U.S. Pat. Nos. 4,273,115 and 4,316,457 pertaining to orthopedic bandages, one uses a polyethylene separator film which is wound together with the bandage to prevent its transformation in a mass at the time of its application. The U.S. Pat. No. 4,143,655 recommends another type of separator having multiple openings whereas the U.S. Pat. No. 4,454,873 allows to eliminate the bothersome effect of a separator by the coating of a nonadherent and hydrosoluble film on the material of the bandage itself. However, the latter solution has the drawbacks of progressive contamination of the water in the preparation hydrocollator and of significant reduction of the interlaminar strength between the various plies in a cylindrical cast in particular.

The second category refers to internal physical adaptations in the material which contains those polyesters. In this way, very high content of up to 50 percent, of mineral fillers, preferably finely divided allow to increase the viscosity of those polyesters in the melt without being able however to prevent a 3 mm thick sheet, for example, to stretch under its own weight. That same sheet, in the melt state does adhere on itself in a way that a mistake in positioning cannot be corrected. The European Pat. EP-A-0 169 037 applies this principle so that the tack is reduced by a selection of fillers at high concentration whereas the stretch in the melt is controlled by the crosslinking of a thermoplastic rubber mixed beforehand according to the third category of adaptations described hereafter. It could be observed also that the type of Raschel knitted web with bulky strands made of shortcut fibers described in the U.S. Pat. Nos. 4,273,115 and 4,316,457 is absolutely necessary to suppress the effect of the to large fluidity of the polycaprolactones and of the linear polyurethanes related to applied in an orthopedic bandage for example. Those largely open strands have a very low apparent density and offer a volume between the fibers of about 80 percent. The U.S. Pat. No. 4,273,115 specifies moreover that the strands of fibers can only be partially impregnated with the polymer. The mechanical strength of those strands necessarily little tied up and partially impregnated is therefore rather weak and that can be seen in particular on the finished product impregnated with the resin and that can be easily torn by hand. The strand elements being so coated with polymer, the entirety is opposed to the fluid flow of the thermoadhesive constituent. However the latter remains highly deformable in a plastic manner, and the use of a roll of this material treated at the right temperature leads rapidly to a dense mass which becomes very hard to unwind if a separator polyethylene film has not been wound in the roll together with the bandage itself.

Finally, the third category of adaptations aims to give the polycaprolactone a resistance to stretch at the utilization temperature, or even an effect of elastic memory, by various means of physical or chemical crosslinking or through mechanical blending with another polymer followed by a physical or chemical crosslinking. Those adaptation techniques of polycaprolactone are described in the U.S. Pat. No. 4,240,415 of L. H. Wartman (chemical crosslinking with electrons), in the U.S. Pat. No. 4,175,177 of J. E. Potts (modification of polycaprolactone in the form of a crosslinkable copolymer), in the U.S. Pat. No. 4,483,333 of L. H. Wartman (blend and physical crosslinking with polyethylene), in the European Pat. No. 0 235 500 of R. L. Mahlon (mechanical blend and physical crosslinking through the hard segments), in the French Pat. No. 2,519,992 of H. Grouiller (blend and chemical crosslinking of polyurethane), in the European Pat. No. EP-A-0 086 686 of H. Grouiller (mechanical blend with a miscible elastomer), in the Patent WO-A-9 109 909 of Polysar (mechanical blend and physical crosslinking by a high Tg terpolymer), in the U.S. Pat. No. 4,326,509 of Usukura (mechanical blend and physical crosslinking due to the crystallinity of the resin added to the linear saturated polyester).

The objectives presently aimed for in the applications based on this know-how are not satisfied neither by these aliphatic polyesters or these polyurethanes related to, nor by the simple blends of polymers described above, particularly if the application concerns the orthopedic bandage in consideration of the excessive amounts of solvents that would be required. Indeed, when the PCL is not crosslinked by the techniques here above, its hot fluidity is such that a sheet elongates under its own weight and its adhesiveness provokes a transfer of matter onto the user's hands and tools without however providing permanent adhesion. Moreover they harden upon cooling, at a rate that does not always allow the user to complete his work without heating again locally or totally.

If one tries to apply the polymers described in the U.S. Pat. Nos. 4,273,115 and 4,316,457 onto a fabric or a knitted web having especially open mesh, and being of high tenacity which is possible if strands are selected being more tightened, better tied up and made of continuous fibers, one must, in order to end up with the same surface weight of thermoadhesive resin, coat to a greater extent the outside part of the strands from which the resin is no longer held by the fibers. It can then move in an undesirable manner and be transferred on the tools or the hands of the user during the application.

Moreover the knitted webs with bulky strands as recommended in those patents are soft to a point that they cannot be handled in a width under about one meter. Under those circumstances already, there is a narrowing of the width caused by the traction and the weight when they are impregnated with the usual vertical processes also described in the same patents. Bandages of usual width are thus obtained in this case, by slitting the product after its impregnation in full width and drying. Such slitting operation results in sharp edges at the point where transverse threads have been cut. There is an obvious interest to obtain a bandage in useful width with uniform edges free of unevenness. However, with the textile construction that is required by the polymers described in the referenced patents, narrow width strips cannot hold themselves sufficiently and the final product comes out substantially narrower than at the beginning. Moreover, one observes concurrently with this type of bulky knitted web made of strands with short fibers, an elongation in the other direction which comes back at the time of heating to prepare the use. Thus the textile substrates necessary for the polymers of the prior art do not allow a dimensionally stable product, and it is necessary to prepare the bandage by slitting after the polymer has been applied. If in other respects, one is interested with those impregnated knitted webs, not in view of a cylindrical cast but in view of splinting sheets or orthoses, the user must take account for the shrinkage, sometimes up to 10 percent, that arises during the preparatory heating of the sheet and this is inconvenient. There is therefore an interest to use less deformable fabrics.

The linear polymers of the prior art are also characterized by thermal properties such as the softening temperature, the melting temperature and the rate of hardening that are well fixed. Due to the specificity of the new needs, it has become necessary to be able to act on those characteristics preferably independently of any other action on rigidity and mechanical strength.

Finally, it could be established that the linear polymers of the prior art in particular experience a physical aging such that after about a year, it is sometimes possible to break by hand a 3 mm thick sheet, the latter being resistant to human strength when it has been freshly molded.

Knowing that the applications of the products envisioned in the present invention comprise a cycle of heating and cooling, it is useful to define at least four characteristic temperatures of which it is also interesting to examine the values to appraise the advantages provided by the invention beyond the simple control of fluidity and adhesiveness.

The softening temperature (T1) is the temperature at which the material starts to lose its rigidity. In particular, it can be determined by the ASTM method No. 1043-87 or 1053-89 taking the inflection point of the curve of variation of modulus with temperature or the temperature at which the modulus of elasticity has dropped by half from its value at 22° C.

The treatment temperature (T2) for the application is the suited temperature at which it is required to bring the material in order that it has in an appropriate time, the desired formability and adhesive characteristics and retains them sufficiently during the time necessary to complete the application. It has to be noticed that during the application, the material cools by either a natural or forced way. Depending on the thickness of the material and the ambient temperature, that T2 temperature will be more or less high, necessarily above the thermodynamic melting temperature of the semicrystalline constituent in the combination.

The temperature (T3) is the temperature at which, during the cooling of the material, normally after completion of the application, the material starts losing its adhesive capability.

The temperature (T4) is the temperature at which, during the cooling of the material, normally after completion of the application, the material starts losing its capability to be shaped due to the increase of its rigidity.

In practice, one refers more often to the time (t3) after which the material is no longer adhesive and the time (t4) after which the material is no longer formable when it cools down in given thickness, in a given ambience and having applied a given treatment temperature. In such case, there is a parallel between t3 and T3 as well as between t4 and T4.

This distinction of the above four temperatures allows to specify the optimal characteristics of the envisioned products from that point of view.

In a general manner, the temperature T1 should be as high as possible above room temperature, temperature T2 should be as low as possible to allow easy application without risk of burns, which is particularly important in the instance of an orthopedic bandage. The temperature T3 should be as low as possible to provide the operator with a maximum delay t3 during the application. The optimal value of T4 depends on the application and on the time t4 the operator wants to have to complete his task. Time t4 must be sufficiently long but not to the point the operator has to wait for the evaluation of his work.

As already said, the linear cyclic ester based polymers of the prior art offer little possibility to change those characteristic temperatures which are rather high with respect to the requirements of the applications. In this manner treatment temperatures of 68° C. to 74° C. are recommended in practice, which causes a problem at the beginning of the use of the material. Temperatures T3 and T4 are high as well so that times t3 and t4 are often too short and especially when a longer time is required before the material which is too hot can be manipulated. In practice, this inconvenience can be overcome with an overall or localized treatment at temperature T2 or higher, but this causes imperfections, inaccuracy and sometimes hardship to operators with little skill.

In summary, there is for each type of application an optimal value of temperature T4 or of the time t4 which depends in particular on the size and the complexity of the work to perform. T1 must be as high as possible and T2, greater than T1, as low as possible, so that a measurement of the efficiency of a material can be translated from the gap between T1 and T2 which must be as small as possible. In the prior art, T3 can only be above T4 because there is always a temperature gradient between the inner part of the material and its surface. There is an advantage to make T3 closer to T4 or t3 closer to t4, and even sometimes to reverse the natural order of these times and temperatures so that adhesion is possible until the last moment of formability.

It is now clear that the characteristics of adhesiveness and of fluidity introduced above have to be taken into account in the time intervals t3 and t4 respectively.

The object of the present invention is to provide materials becoming easily malleable and moldable by hand up to large sizes of a meter or two, after a treatment at the lowest possible temperature under 100° C. while retaining the properties at room temperature up to a temperature as high as possible above room temperature.

Another object of the present invention is to provide those materials in the form of thermoplastic orthopedic bandages, lightweight and aerated, exhibiting, without having to count on an inter-layer separator film, a good interlaminar strength, a good rigidity and a good resistance to tearing, such that the roll does not transform in a dense mass nor transfer the resin on objects other than itself during its hot application.

Another object of the present invention is to provide also those materials in the form of bandages soft or semi rigid that can be laminated after some temperature treatment and that become non sticky again when cold.

Another object of the present invention is to provide those materials in the form of recyclable plaques about 3 mm thick, with or without openings and which after treatment at a temperature under 100° C., let themselves be formed and deformed in a stable manner, not being deeply imprinted by the fingers, and adhering on themselves in a way they can be taken apart if necessary without leaving significant marks, and which have a rigidity characterized by a flexural modulus of at least 500 MPa.

Another object of the present invention is to provide this same type of plaque with variable rigidity or flexibility characterized by a flexural modulus from 50 to 600 MPa in the absence of fillers.

Another object of the present invention is to provide those materials in the form of composite or non composite plaques or sheets easily moldable and adhesive to themselves, and which retain their shape as the molding progresses without risk of uncontrolled deformation either due to exaggerated fluidity or to an effect of elastic memory, so that a single operator can laminate a large size part such a lombostat, a stage scenery or the negative print of an object on the average larger than a meter.

Another object of the present invention is to provide those materials under the form of thermoadhesive masses, soft or rigid and with fast setting time, able to bind rough objects or objects offering uneven surfaces and adhering to them at a temperature at which they are easily manipulated.

Another object of the present invention is to obtain those thermoadhesive materials such that they can be adhesive as long as they are malleable.

Another object of the present invention is to obtain those materials with inexpensive processes using as little as possible or no solvent.

Another object of the present invention is to make those materials recyclable and reusable.

In the present invention, one has obtained several means to control the fluidity, the adhesiveness, the rigidity and the characteristic temperatures of thermoadhesive materials in the form of mass granulated or not, plaques, sheets or yet textiles with or without open mesh coated with such materials, formable and moldable under the conditions described above, of an easy working at a temperature that does not impede manual application in particular.

According to the present invention, it was found surprisingly that some IPN type combinations, that is to say, wherein at least one of the constituents is synthesized in the presence of the other, and combining an amorphous or semi-crystalline polymer structure that has in the combination a viscoelastic to rubbery behavior above a certain temperature still under 80° C., with a varying proportion depending on the application, of thermoplastic polymer structure, essentially semi-crystalline and comprising a minimum amount of aliphatic ester structural units, being themselves relatively fluid when they are not engaged in the combination, allow to overcome the difficulties cited above of a to large fluidity and of excessive adhesiveness, while providing new possibilities to vary those characteristics as well as other useful characteristics in the application or use of resulting materials such as the rigidity and the temperatures T1, T2, T3 and T4.

In the continuation of this description, one will name "first constituent" and "second constituent", the two above defined constituents of the combination respectively.

The combination of the present invention comprises a first amorphous or semi-crystalline polymer constituent that is above its heat softening point at least at the temperature T2 and exhibiting at that temperature at least a viscoelastic to rubbery behavior, and an essentially semi-crystalline second constituent with a content of aliphatic ester type structural units of at least 80 percent and exhibiting at the temperature T2, an essentially plastic behavior, and such that, one at least of the two constituents having been synthesized in the presence of the other, one ends up with a morphology of semi-IPN type, thermoplastic IPN or homo-IPN.

It has been found indeed that those combinations, very distinct from simple mechanical polymer blends, provide new properties often unattainable with those blends. According to the topology defining IPNs, it has been observed also that these new combinations exhibit a typical morphology that can be seen in particular by electronic microscopy and by dynamic mechanical analysis and which is not closely connected to the one of the blends described in the prior art.

The combinations as described here before were found to be thermoadhesive in a fully satisfactory manner, without showing the inconvenience of uncontrolled viscous deformation. Through the selection of the proportion and the elements of the first constituents, and also to some extent by the selection of the elements of the second constituent, it has been observed that it was also possible to adjust the characteristic temperatures, the flexibility during the application and the rigidity of the finished product according to the needs.

According to the present invention, the second constituent is selected such that it has intrinsic thermoadhesive properties whereas the first constituent does not have them necessarily. Inversely, one has found that the first constituent has to provide the combination with a viscoelastic behavior when it is subjected to the temperature of the preparation treatment, which has been obtained with some first constituents having themselves a viscoelastic to rubbery behavior whereas the second constituent is only plastic at the same temperature.

In this manner, it was surprising to note that some combinations comprising from about 15 to about 50 percent of, for example, polyhexylmethacrylate, polyisobutylmethacrylate, polybutylmethacrylate, polyethoxyethylmethacrylate, or polyvinylacetate as the first constituent, and from 85 to 50 percent of polycaprolactone or of another polymer comprising at least 80 percent of aliphatic ester structural units as the second constituent, have a rigidity and a thermoadhesive ability sufficient to provide a suited interlaminar strength in a bandage or a splint based on a pressed plaque or based on impregnated cloth, even when mechanical blends of 80 percent of polycaprolactone and 20 percent of an ethylene vinyl acetate copolymer with a content of 28 percent in acetate, do not show this important adhesive ability. This is even more surprising considering that the ethylene vinyl acetate copolymers are known to be "hot melt" adhesives whereas the polymers that were used here are not.

Similarly, combinations obtained by the synthesis of polyethyldiglycolacrylate, for example, in proportion 10 to 60 percent in an amount of from 90 to 40 percent of a linear polymer based principally on polycaprolactone, give a fast setting thermoadhesive product whose flexibility at room temperature increases with the proportion of acrylate. In addition, it was interesting to note that the combinations based on those first constituents based on vinyl or (meth) acrylates can be applied validly on a knitted web with open mesh and by using 3 to 4 times less of solvent than the quantity required when proceeding according to U.S. Pat. No. 4,316,457.

It was also found that certain intramolecular combinations of the type of linear, branched, or graft, or block copolymers, not having a gel fraction greater than 50 percent, are suited the same manner if the copolymer comprises blocks or grafts of the type of semi-crystalline aliphatic polyester having a melting temperature between 35° C. and 80° C. and an individual molecular weight of at least 3000 being in amount of at least 50 percent, said blocks defining the second constituent, and blocks, grafts, or branches, whether semi-crystalline or not, but having a viscoelastic to rubbery character at least at the melting temperature of the second constituent define the first constituent. From a nomenclature point of view, this type of combination corresponds to a homo-IPN.

In particular, it was found that polyurethane preparations based on a polyester diol with a molecular weight from 2500 to 5000, a triol whose hydroxyl equivalents are in proportion of about 3 to 15 percent of the total of hydroxyls and a diisocyanate like toluene diisocyanate or hexamethylenediisocyanate in proportion of about 92 to 98 percent with respect to stoechiometry give the desired results from the point of view of controlled fluidity and adhesiveness. Depending on the proportions mentioned above, this material is either soluble and shows a molecular weight distribution unusually large with a significant fraction above 50000, or has an insoluble fraction up to 50 percent which does not suppress the general desired characteristics.

Another interesting intramolecular combination has been found by preparing a block urethane copolymer by reaction of 5 to 15 percent by weight of rubbery polyols such as polytetramethyleneglycol or polypropyleneoxide diol or polyol in the presence of polyester diol of molecular weight of 3000 to 4500 with a diisocyanate in proportion near stoechiometry, the highest rigidity at room temperature being obtained with a polytetramethyleneglycol with a mass at least equal to 2900. By increasing the proportion of rubbery polyol up to 50 percent, one still obtains a thermomalleable and thermoadhesive material that becomes more flexible when the proportion increases.

In a first group of polymers used as the first constituent, the vinyl and the acrylic or methacrylic esters polymers and copolymers appeared to be particularly interesting.

The preferred embodiment of the present invention is thus to synthesize at least one of the two constituents is the presence of the other, or even to synthesize both of them at the same time from a mixture of all the reagents but using two different reaction mechanisms. In this fashion, one obtains, through a process in bulk, in solution or in aqueous dispersion, a polymer alloy where the two constituents are dispersed one into the other in a quasi co-continuous manner. This type of alloy structure corresponds in principle to the definition of interpenetrating polymer networks (IPN) or to the definition of thermoplastic IPN, according to L. H. SPERLING in "Interpenetrating Polymer Networks and Related Materials", Plenum press 1981, pages 3, 39 and 99. One could conceive that in some cases, the same result could be obtained with a simultaneous dissolution of the two polymers in a solvent to be evaporated later, but one imagines easily that this technique subjected to molecular segregation would be uneconomical and have negative environmental impact. Finally, the direct mixing by blending the two constituents as they are defined, gives only rise to a discrete morphology of one phase dispersed in the other unless the two constituents are totally miscible.

In a second group of polymers used as the first constituent, it was found that it was possible to obtain the same effects with a copolymer such as, for example, of the polyurethane or polyurea type which has a viscoelastic to rubbery behavior at least at temperature T2 and in the interval T2 to T4, and eventually under T4 depending on the fact that the characteristics of this polyurethane govern the temperature T4 or that the latter is governed by the characteristics of the second constituent respectively.

One obtains this constituent being viscoelastic to rubbery at least a temperature T2, by reaction of a mixture of diol, triol and diisocyanate in particular, but one can obtain it also from bifunctional reagents, only if one of them is intrinsically rubbery like polytetramethyleneglycol or a polypropyleneoxide. One can obviously use at the same time a triol and a rubbery diol.

This second type of first constituent of polyurethane nature, can moreover be amorphous or semi-crystalline at room temperature but in this latter case, its softening temperature must be under the envisioned T2 temperature, thus in any case under about 95° to 100° C. and preferably under 40° C. It goes without saying that the urethane reaction is not indispensable to form this type of first constituent in the intramolecular combination, and that any other chemical link can be suited.

In a preferred embodiment of the invention according to this second family of first constituents, in particular if one seeks to obtain at room temperature a rigidity as high as possible, one chooses a polyurethane containing at least about 50 percent of crystallizable structural units and having a melting temperature under T2, such as based on an aliphatic ester having a molecular weight of at least about 2000 and preferably above 3000.

As well as for the first family of first constituents, one obtains the best results by synthesizing at least one of the two constituents in the presence of the other or even the two together. The resulting alloy structure can also be qualified as thermoplastic IPN or even thermoplastic homo-IPN.

A particularly advantageous combination of this type is obtained by polymerization of a reactive mixture comprising an identical crystallizable moiety with molecular weight equal to at least 2000 that splits into the two constituents. In a preferred manner, this identical moiety is an aliphatic ester diol such as polycaprolactone diol or a polyhexamethyleneadipate diol for example, reacting either in the presence of a triol and of a diisocyanate in amount of a few percent, or even 10 percent under stoechiometry, or in the presence of a polytetramethyleneglycol of a molecular weight of at least 2500 or a polypropyleneoxide diol of about the same weight and of a diisocyanate in practically stoechiometric proportion. Some proportions between the crystallizable diol and the triol or between the crystallizable diol and the polytetramethyleneglycol or polypropyleneoxide diol give the desired effect for the viscoelastic behavior while opposing to fluid flow.

Among these combinations, one includes also the intramolecular combinations of the type of block copolymers where the rubbery segments based on polytetramethyleneglycol have a molecular weight at least equal to 2500.

These combinations bear several decisive advantages in particular with respect to cyclic ester polymers alone, as well as to linear urethane homopolymers of the prior art which as recalled above which require the type of substrate with bulky strands as well as a separator film for the winding of orthopedic bandage rolls.

It should also be noted that the present invention enlarges considerably the spectrum of resulting applications. It allows in particular to obtain a soft thermoadhesive bandage that proves to be useful for the treatment of a dislocation such as of the tendons. It also allows thermoadhesive masses with variable rigidity or flexibility with a fast setting time, used as thermoadhesive films or sheets with a thickness up to choice allowing in particular to fill cavities at the surface of rough bodies such as concrete or bricks. In addition, thermoformable plaques and sheets that can be further welded from place to place by localized heating are provided.

According to the terms of the present invention, and in particular when the second constituent having a thermoadhesive character is itself a linear or branched but not crosslinked polyurethane, for example, by the reaction of a diisocyanate with an aliphatic ester type diol in the presence of the reaction giving the rubbery polyurethane based in part on the same aliphatic ester diol, this combination of polyurethane obtained is distinct from a homopolymer and in particular from a linear homopolymer by the character that the second constituent can in principle be extracted. It can be a sol-gel type separation as it can bear on a distinction from chromatography or simply a distinction based on the mass balance of the reactive moieties that necessarily leads to the formation of two distinct species.

One can moreover observe the novelty that the heterogeneous character of the material giving the desired effect is obtained by following in particular a process generally avoided in the art of urethane elastomers as well as in the art of thermoplastic polyurethanes with high melting point. In the present invention, one may react, for example, a mixture of polycaprolactone diol of weight 4300 with a small quantity of a polycaprolactone triol and a diisocyanate such as hexamethylenediisocyanate in quantity under the stoechiometric ratio by about 3 to 10 percent depending on the quantity of triol that is used. In such case one observes that the product is viscoelastic when hot and keeps a good thermoadhesive ability. This is lost if the isocyanate is in a stoechiometric proportion, in which case, the material becomes purely elastomeric which corresponds to the practice of the polyurethane elastomers.

One can easily evaluate the viscoelastic character obtained by the present invention observing in the temperature interval T2 to T4, a partial retraction of the material after elongation. The linear polyesters or the resulting linear polyurethanes exhibit in those same conditions a fluid deformation without retraction, whereas those polyurethane when crosslinked have a retraction of 100 percent being at the same time less deformable and non adhesive.

In summary, the material's characteristics obtained with the second family of the first constituent are such that one finds a plastic contribution and a viscoelastic to rubbery contribution, the combination being itself viscoelastic.

From the point of view of the process used to obtain the material, one finds an important advantage over the process described in the U.S. Pat. No. 4,316,457, because it is no longer necessary to polymerize in two steps as required to obtain the linear urethane homopolymer. In contrast, it was surprisingly found to be easier to obtain the desired properties when the heterodispersed character of the material is more pronounced.

As another advantageous consequence on the physical characteristics of the product, it has been shown that the temperatures T2 necessary with these intramolecular combinations are from 5° to 10° C. under those required for the cyclic ester polymers or the linear polyurethanes of the prior art, whereas temperatures T1 are interestingly diminished by 1 to 4 degrees only. Moreover the time t4 is thereby lengthened, going for example from about 1 to 2 minutes to about 3 to 6 minutes. This becomes an important advantage for the user with little skill or having to perform a large size operation.

In a general manner, the applications of the products of the present invention are much larger than those of the prior art. One can obtain materials that are easily worked by hand into circular casts, orthoses, external and supporting prostheses, as well as soft thermoadhesive bandages which were not previously known. Furthermore, large size decorative structural elements are possible.

The thermoplastic orthopedic bandages in particular can be directly fabricated in useful widths of 5, 10, and 15 centimeters for example and be finished with smooth and uniform edges. The thermoplastic splints and orthoses obtained by impregnation of a web can be, according to the present invention, dimensionally stable for the latter allows to use knitted webs with continuous fiber threads which are rather entangled, thereby preventing elongation during the impregnation process.

The present invention allows one to vary the characteristic temperatures in a much larger range than with the prior art and obtain variable flexibility's and rigidities of the material not only during its application but also after it has set.

EXAMPLES

1. In a beaker, one has mixed 100.5 g of polycaprolactone diol of molecular weight 4280, 3.9 g of hexamethylenediisocyanate, 34.6 g of butylmethacrylate, 0.03 ml dibutyltindilaurate and 0.4 g of Trigonox 21. The mixture has been poured in an aluminum cup and placed in the oven at 90° C. One has obtained a mass which after cooling was hard and rigid. The product has been reheated at 80° C. and molded in the press in 3 mm thickness. Treated at 60° C., the plaque can easily be shaped and does not flow under its weight.

2. The preparation as described in example 1 has been diluted in 70 parts of methylethylketone for 100 parts of resin. The solution has been applied by a dipping process on a polyester/cotton web with 6 mm mesh size and weighing 151 g per square meter. By oven treatment at 95° C., one obtains a bandage whose 75 mm width allows to obtain a roll directly by a winding process. After dipping in a water bath at 60° C., one can easily unwind the roll and apply the bandage on a limb. The bandage hardens in 5 minutes.

3. In a preparation according to example 1, one has used 43 g of butylmethacrylate instead of 34.6 g. The material examined by DSC shows a degree of crystallinity of 76.91 percent whereas the same preparation without the methacrylate constituent has a degree of crystallinity of 68.48 percent. This means that in the combination, the second constituent surprisingly crystallizes to 97 percent of its content. On a press molded plaque in 3 mm thickness, one measures an efficient tensile strength of 9.6 MPa and an elongation at break of 28 percent. The modulus of elasticity is 512 MPa at 22° C. and the characteristic temperatures T1 and T2 are respectively 49° C. and 60° C. whereas for the prior art known as HEXCELITE, those temperatures are 52° and 70° C. respectively.

4. Following examples 1 and 3, one has replaced the butylmethacrylate, successively by 2-ethylhexylmethacrylate (2EHMA), 2-ethylhexylacrylate (2EHA), hexylmethacrylate (HMA) and isobutylmethacrylate (MAISOBU) varying also the proportions by weight between the first and the second constituent as indicated in Table 1 hereafter. One finds the indicated values for different important properties which show the diversity of the possible applications. One sees again that the first constituent influences deeply the degree of crystallinity of the second constituent, a totally unexpected phenomenon that impacts the physical properties. One compares also to the properties of the second constituent taken alone.

TABLE 1

| Proport | Flexural Modulus (MPa) | Mechanic Strength (MPa) | Cryst in IPN (p cent) | Cryst in ester (p cent) | T2 (°C.) |
|---|---|---|---|---|---|
| 2EHMA 30–70 | soft | 8.58 | 52.05 | 74.4 | 60 |
| 2EHA 30–70 | soft | 8.65 | 58.78 | 83.9 | 55 |
| 2EHA 40–60 | 63 | 6.88 | | | 55 |
| 2EHA 50–50 | 72 | 5.15 | | | 55 |
| HMA 30–70 | 104 | 8 | 51.79 | 74 | 60 |
| MAISOBU 30–70 | 457 | 14.5 | 57.3 | 81.9 | 60 |
| MAISOBU 40–60 | 479 | 16.5 | | | 60 |
| MAISOBU 50–50 | 531 | 16.86 | | | 60 |
| none 0–100 | 518 | 12.7 | 68.48 | 68.48 | 70 |

5. Following the procedure of example 1, one has replaced butylmethacrylate by ethylglycolmethacrylate and finally by ethyltriglycolacrylate. One obtains the same type of material which becomes softer and softer by changing the monomer in the indicated order. The material is a good adhesive at the temperature of 55° C. and becomes non-tacky again after cooling to room temperature.

6. One has prepared a formulation which is adhesive on concrete like this. In a beaker, one mixes at 65° C., 200 g of polycaprolactone diol of weight 4280, 8.4 g of toluenediisocyanate and 52.1 g of either butylmethacrylate (MABU) or butylacrylate (ABU), and 1 ml of Trigonox 21 and 0.09 ml of dibutyltindilaurate. The mixture is poured on a nonwoven fabric made of polyester weighing 110 g per square meter in the frame of a press having a thickness of 1.5 mm and heated at 65° C. for 30 minutes then at 100° C. for 30 minutes. After cooling, one obtains a rigid and dry sheet that one applies on a concrete block heating at 80° C. and applying a pressure of 1 Kg per square centimeter and having taken care of leaving 15 cm of dry sheet for a peeling test according to ASTM method 903-49. The latter gives an energy at failure beyond 7960 J/m2 for the MABU and beyond 10,000 J/m2 for the ABU, whereas the second constituent applied alone gives an energy at failure of 6080 J/m2. One has reproduced this experience taking weight ratios of the first to the second constituent of 30/70, 40/60, 50/50. In all cases, except for 50 percent ABU, one has observed a remarkable mechanism of cohesive failure in the concrete. One has also observed that the curves of elastic modulus with respect to temperature measured by dynamic mechanical analysis present a totally unexpected evolution. On one hand, with 20 percent ABU, the modulus is at all times greater than the modulus of the second constituent taken alone, which is surprising since polybutylacrylate is a rubber with a glass transition temperature at (−45° C.). On the other hand, with the various amounts of MABU, the modulus is greater than that of the second constituent taken alone up to a temperature of about 33° C. and to a greater extent with MABU content. Above this point there is crossover of the curves and reduction of the temperatures T1 and T2 when the MABU content further increases. This means that, by comparison with the second constituent alone, one now obtains a stiffer material at room temperature but which softens and can be applied at a lower temperature. This effect totally opposite of the results obtained with mechanical blends with which a reduction of the transition temperature always accompanies a reduction of the modulus at room temperature. One has obtained the evidence of a characteristic IPN morphology by observing under the electron microscope an ultra thin cut from the 50 percent MABU compound. One clearly sees the topology of the phase concentrated in MABU that shows network like pattern within the ester rich phase.

7. On a 75 mm wide knitted web as described in example 2, one has applied by impregnation, a solution in methylenechloride whose quantity has been adjusted to obtain a viscosity of 150 centipoise at 25° C., comprising 483.8 g of polycaprolactone diol of weight 4280, 3.4 g of polycaprolactonetriol having an equivalent weight of 184, 19.7 g of hexamethylenediisocyanate and 0.15 ml of dibutyltindilaurate. After treatment in an oven at 95° C. for 40 minutes and cooling, one obtains a bandage which, winded in a roll without separator can be treated in water at 65° C., then unwound to apply it on a limb without having transfer of matter on the fingers of the operator. The same type of bandage treated by the operations giving the linear polyurethane described in the prior art gives rise to undesirable resin transfer onto the hands of the operator. After treatment at temperature T2, one observes that the resin applied on the substrate yields in a viscoelastic manner and that it is necessary to apply a certain force to take it away.

8. Following the technique described in example 2, one has impregnated also some 10 cm wide gauze cloth which after treatment in an oven has been laminated in 4 layers under the heated press to provide a thickness of about 3 mm, and in 3 layers to provide a thickness of about 2 mm. These laminates were used respectively to measure the flexural modulus at 22° C. and to monitor the change in torsion modulus with time, under ambient conditions, after treatment at 70° C. for 90 seconds. Both measurements were made along the direction where the gauze itself has no mechanical resistance. The second measurement allows the determination of the times t3 and t4. One has also laminated the impregnated knitted web in 4 layers following the technique for orthoses preparation. These specimen, tested in flexion also, offer as desired, a macroscopic porosity from 0.30 to 045. One has obtained the following properties compared in Table 2 with those obtained for the same knitted web and the same gauze cloth impregnated with the linear polyurethane of the prior art.

TABLE 2

| First constit | Second constit | Flexural modulus (knit) (MPa) | Flexural modulus (gauze) (Mpa) | t3 (min) | t4 (min) |
|---|---|---|---|---|---|
| none | lin.PU | 716 | 481 | 3.4 | 7.3 |
| 20MABU | 75 | 640 | 446 | 3.1 | 6.0 |
| 20MABU& 5MAEE | 75 | 766 | 444 | 5.5 | 8.75 |

One clearly sees that it becomes possible to shorten or to lengthen the working time by comparison with the prior art without modifying the rigidity. In this domain indeed, the user is able to vary the working time in the order of one minute.

Having thus described my invention, I claim:

1. A molecular or intramolecular combination of materials of the form of an interpenetrating polymer network, wherein one of the constituents is synthesized in the presence of the other, and comprising a first polymer constituent which is amorphous in the temperature domain above 40° C. and having in said combination, a behavior between viscoelastic and rubbery behavior at a temperature under 80° C., and a second semi-crystalline constituent comprising 80 percent at least of the recurring unit of one or several polyesters having an average crystalline melting temperature comprised between 35° C. and 80° C., characterized in that the first constituent is either selected among the polymers or copolymers comprising vinyl, acrylate, or methacrylate moieties or their mixtures and form with the second constituent a blend of macromolecules or selected among the group of polyurethanes and form with the second constituent an intramolecular combination of distinct macromer segments.

2. A combination according to claim 1, wherein the two noncrosslinked constituents are partially or totally miscible in a morphology of a thermoplastic semi-interpenetrating polymer network.

3. A process for producing the combination described in claim 2, characterized in that the second noncrosslinked and noncrosslinkable constituent is dissolved in the mixture of monofunctional monomers of the first constituent with or without the aid of a solvent, said monomers are brought to polymerize by any means of polymerization in bulk, in solution or after such preparation has been placed in contact with a textile substrate.

4. A process according to claim 3, wherein the means of the combination are applied onto a textile substrate and brought to polymerize afterwards.

5. A process for producing the combination described in claim 2, wherein the second constituent is synthesized in the presence of the first one or of the means to obtain the first one, with or without the aid of a solvent, by reaction of a mixture of polyisocyanates and polyols, said polyols containing an amount of at least 80 percent of semi-crystalline polyester macromer segments having an individual average molecular weight of at least 2500 and said polyols having an average functionality not exceeding 2.5.

6. A combination according to claim 1, wherein the first constituent partially or totally crosslinked at and distinct from the second forms with the second noncrosslinked constituent a dispersion partially or totally miscible in a morphology of a thermoplastic interpenetrating polymer network.

7. A process for producing the combination described in claim 6, characterized in that the second noncrosslinked and noncrosslinkable constituent is dissolved in the mixture of monomers of the first constituent comprising a small amount not exceeding 5 percent of multifunctional monomers with or without the aid of a solvent, said monomers are brought to polymerize in bulk or is solution or after the preparation has been placed in contact with a textile substrate.

8. The process according to claim 7, wherein the polymerization causes the crosslinking of the first constituent.

9. The process according to claim 7, wherein the crosslinking of the first constituent is postponed after transformation of the combination or after its processing on a textile substrate.

10. A combination according to claim 1, wherein the first constituent partially or totally crosslinked and distinct from the second, forms with the second partially crosslinked constituent a partially or totally miscible dispersion in a morphology of an elastomer interpenetrating polymer network when the second constituent is in the melt state.

11. A process for producing the combination described in claim 10, characterized in that the second partially crosslinkable constituent is dissolved in the mixture of monomers of the first constituent comprising a small amount not exceeding 5 percent of multifunctional moieties with or without the aid of a solvent said monomers being brought to polymerize by any means of polymerization and said second constituent being caused to crosslink partially.

12. The process according to claim 11, wherein the crosslinking of the two constituents takes place during polymerization.

13. The process according to claim 11, wherein the crosslinking of at least one of the two constituents is postponed until after transformation of the combination or after its processing on a textile substrate.

14. A process for producing the combination described in claim 10, wherein the second constituent is synthesized in the presence of the first one or of the means to obtain the first one, with or without the aid of a solvent, by reaction of a mixture of polyisocyanates and polyols, said polyols containing an amount of at least 80 percent of semi-crystalline polyester macromer segments having an individual average molecular weight of at least 2500 and said polyols having an average functionality greater than 2.1.

15. A process according to one of claims 3, 4, 5, 7, 8, 9, 11, 12 and 13 wherein the means of the combination are dispersed in an aqueous medium with the aid of polymeric or nonpolymeric emulsifying agents and are brought to polymerize partially or totally in emulsion.

16. A composite material comprising a textile substrate end a molecular or intramolecular combination of materials in the form of an interpenetrating polymer network, wherein one of the constituents is synthesized in the presence of the other, and comprising a first polymer constituent which is amorphous in the temperature domain above 40° C. and having in said combination, a behavior between viscoelastic to rubbery behavior at a temperature under 80° C. and a second semi-crystalline constituent comprising 80 percent at least of the recurring unit of one of several polyesters having an average crystalline melting temperature comprised between 35° C. and 80° C., characterized in that the first constituent is either selected among the polymers or copolymers comprising vinyl, acrylate, or methacrylate moieties or their mixtures and form with the second constituent a blend of macromolecules, or selected among the group of, polyurethanes and form with the second constituent an intramolecular combination of distinct macromer segments, characterized in that the combination is prepared according to claim 15 and is applied onto the substrate from which the water is brought to evaporate and on which the polymerization is carried on to completion.

17. An intramolecular thermoplastic combination according to claim 1, wherein anyone of the two constituents is grafted onto the other.

18. An intramolecular thermoplastic combination according to claim 1, wherein the two constituents are distributed in a branched polyurethane or polyurea at most partially crosslinked characterized by at least 50 percent by weight of semi-crystalline polyester recurring units distributed in linear ester-urethane blocks having an average molecular weight of at least 15000.

19. The combination according to claim 18, wherein the combination has a gel fraction from 0 to 30 percent.

20. The combination according to claim 18, wherein the combination has a gel fraction from 5 to 50 percent.

21. A process to obtain the combination according to claim 18, wherein a mixture of polyisocyanates and polyols is brought to polymerize in a proportion such that the functionality is comprised between 2.05 and 2.25 and the stoechiometry is comprised between 0.98 and 0.90.

22. An intramolecular thermoplastic combination according to claim 1, wherein the two constituents are distributed in a urethane or urea block copolymer characterized by at least 50 percent by weight of semi-crystalline polyester recurring units distributed in linear ester-urethane blocks having an average molecular weight of at least 15000.

23. The combination according to claim 22, wherein the first constituent based on polytetramethyleneoxide or polypropyleneoxide accounts for 5 to 15 percent in the combination.

24. A bulk material or sheet, thermoadhesive by treatment at a temperature under 100° C. that further sets under cooling in a time less than 20 minutes and comprising the combination described in claim 1.

25. An orthopedic or supporting bandage comprising the combination described in claim 1, formable and moldable after treatment at a temperature not exceeding 80° C.

\* \* \* \* \*